United States Patent [19]
Zartman

[11] Patent Number: 4,620,534
[45] Date of Patent: Nov. 4, 1986

[54] APPARATUS FOR INSERTION OF AN INTRAVAGINAL ARTICLE

[75] Inventor: David L. Zartman, Worthington, Ohio

[73] Assignee: New Mexico State University Foundation, Las Cruces, N. Mex.

[21] Appl. No.: 667,132

[22] Filed: Nov. 1, 1984

[51] Int. Cl.⁴ .............................................. A61F 5/46
[52] U.S. Cl. ..................................... 128/127; 604/14; 604/15; 604/16
[58] Field of Search ............... 128/128, 129, 127, 130; 604/11, 12, 13, 14, 15, 16

[56] References Cited

U.S. PATENT DOCUMENTS

| | | | |
|---|---|---|---|
| 2,945,491 | 7/1960 | Gibbs | 128/636 |
| 3,017,879 | 1/1962 | Sapit et al. | 128/636 |
| 3,037,496 | 6/1962 | Melges | 128/636 |
| 3,117,569 | 1/1964 | Wegner | 128/636 |
| 3,429,314 | 2/1969 | Stump | 604/15 |
| 3,760,808 | 9/1973 | Bleuer | 604/14 |
| 3,789,835 | 2/1974 | Whitman | 128/6 |
| 3,842,826 | 10/1974 | Nolan | 128/130 |
| 4,013,066 | 3/1977 | Schuster | 128/2 R |
| 4,157,709 | 6/1979 | Schuster et al. | 604/14 |
| 4,194,503 | 3/1980 | Csatary | 128/130 |
| 4,361,150 | 11/1982 | Voss | 604/15 |
| 4,479,791 | 10/1984 | Sprague | 604/14 |

Primary Examiner—Gene Mancene
Assistant Examiner—Cary E. Stone
Attorney, Agent, or Firm—Lane & Aitken

[57] ABSTRACT

An apparatus for insertion of an intravaginal article into a mammalian female comprises a sleeve, a tube movably received within the sleeve, and a plunger adapted to release an intravaginal article from the tube. An anterior portion of the sleeve is adapted to be inserted within a segment of the reproductive tract of the female that is adjacent to the vulva and an anterior portion of the tube is adapted to be inserted within the tract to a point deeper than the segment, such that contaminants in the segment are not carried to the deeper point by the tube. A method for inserting an intravaginal article is also described.

18 Claims, 8 Drawing Figures

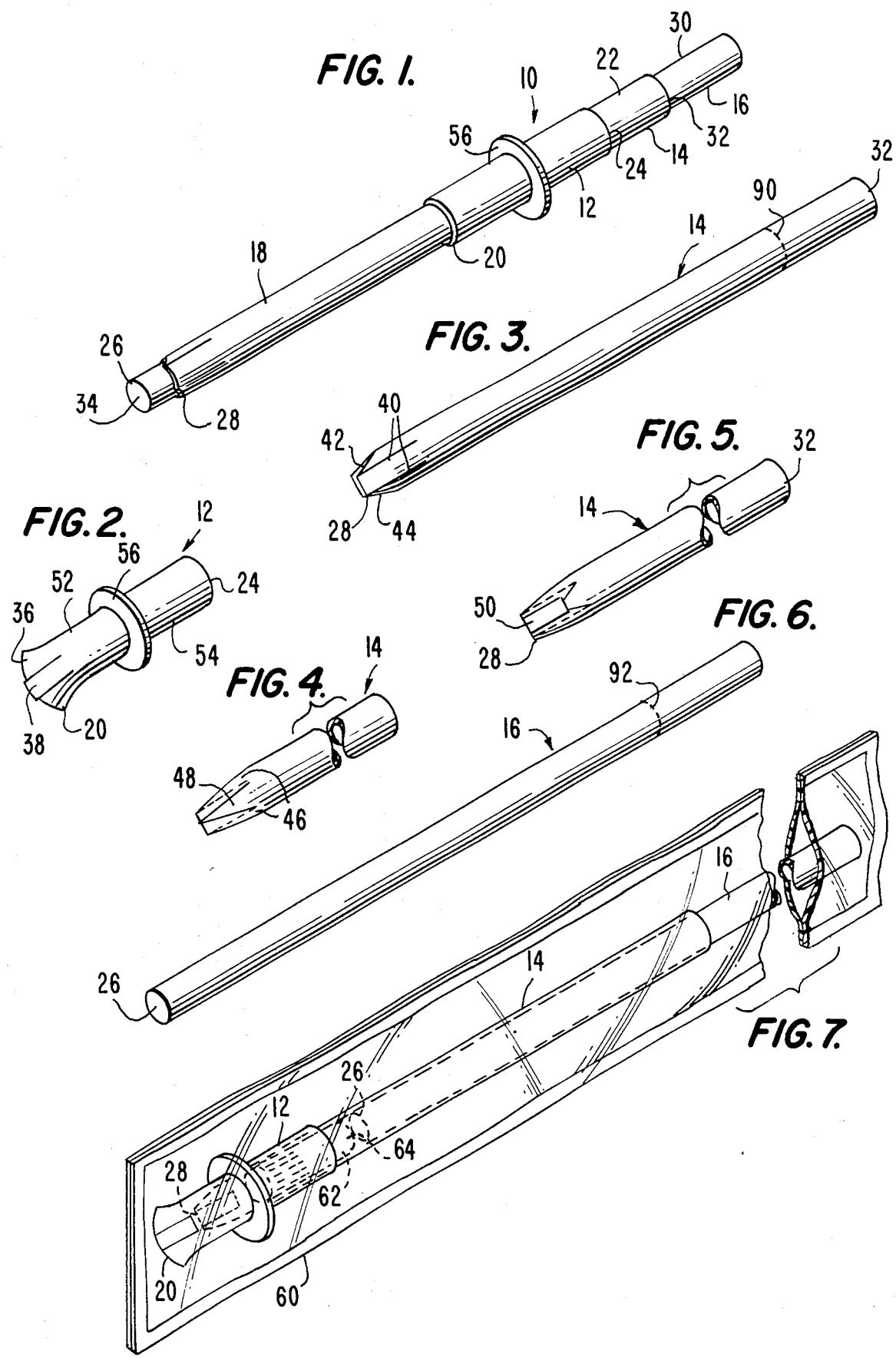

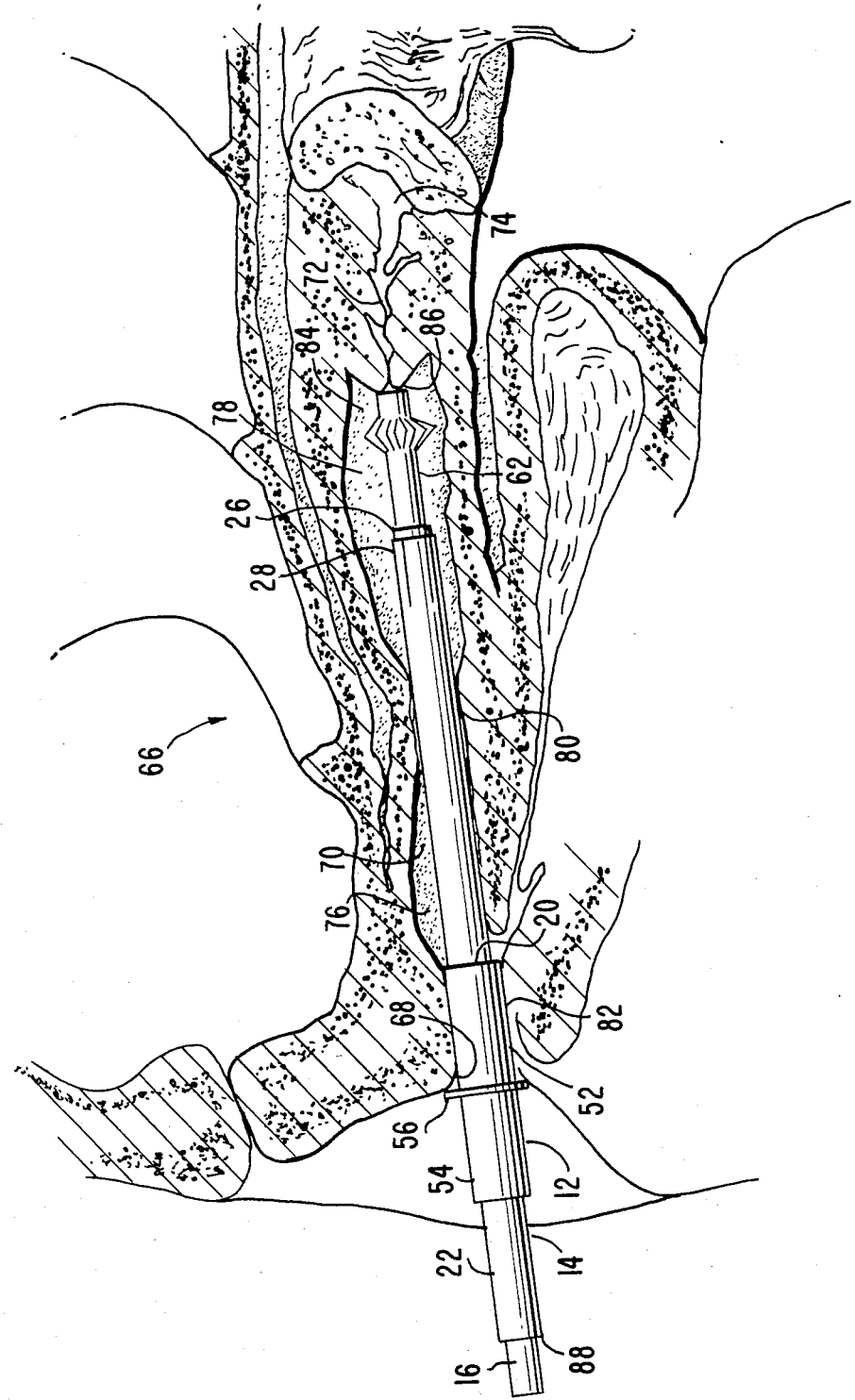

APPARATUS FOR INSERTION OF AN INTRAVAGINAL ARTICLE

BACKGROUND OF THE INVENTION

I. Introduction

This invention pertains to an apparatus for the insertion of an intravaginal article into the vagina of a mammalian female.

II. Description of the Prior Art

A number of apparatus and methods are known in the prior art for inserting intravaginal articles into mammalian females. The common tampon is typically inserted with a cardboard syringe. Certain devices that are used for the vaginal introduction of hormones in farm animals are inserted by hand. Growth stimulators for farm animals, such as the well-known "HEI-GRO" growth stimulator, and sponge pessaries are typically inserted by manually loading the stimulators or pessaries, one by one, into a simple tube that is inserted into the vagina, whereupon they are pushed out of an end of the tube with a rod.

None of the apparatus or methods of the prior art provide an effective means of controlling the risk, especially in the case of farm animals, of carrying contaminants from a segment of the reproductive tract adjacent to the vulva to an area deep within the animal's vagina. The prior art apparatus also fail to provide a suitable insertion means for minimizing the discomfort commonly attendant the insertion process. Further, insertion apparatus typically do not provide means for controlling the depth of insertion of the intravaginal article nor do they enable a means for inspection of the recipient animal's reproductive tract.

The problems associated with the means for inserting "HEI-GRO" growth stimulators are illustrative. The use of the simple tube, through which a plunger rod forces an intravaginal device, is commonly known to result in infection. One independent research team has reported that "Considerable scarring and infection of the vagina were noted with the use of HG ["HEI-GRO"]. . . . Twenty one percent of the HG heifers were rated as having severe infection in the vagina." J. P. Goodman et al, "Effect of Intravaginal Devices and Synovex-H Implants on Feedlot Performance, Cyclic Activity and Reproductive Tract Characteristics of Beef Heifers", *J. Animal Sci.*, 54:491–495 (1982). Another independent research team reported that "The only consistent effect of the 'HEI-GRO' implant was the appearance of a discharge from the vulva which contained large numbers of *Corynebacterium pyogenes.*" R. J. Etches et al, "The Effects of the "HEI-GRO" Device on Finishing Heifers," *Can. J. Animal Sci.*, 59:791–797 (1979). These problems resulted despite the facts that the research teams followed the manufacturer's instructions regarding insertion and immersed the "HEI-GRO" devices and insertion tubes in disinfectant between uses.

Accordingly, it is an object of the present invention to provide an apparatus and method for the insertion of an intravaginal article without introducing pathological contaminants into the recipient animal's contaminant-free reproductive tract or, when such contaminants are already present at the region of the animal's vulva, without introducing the contaminants into a deeper portion of the tract.

It is a further object of the invention to provide an apparatus and method for the insertion of an intravaginal article that obviates the need for first washing the vulva of the recipient animal.

It is a further object of the invention to provide an apparatus and method for the insertion of an intravaginal article that reduces the discomfort and increases the ease of such insertion.

It is a further object of the invention to provide an apparatus and method for the insertion of an intravaginal article that provides a means for the inspection of walls of the reproductive tract of the recipient animal.

It is a further object of the invention to provide an apparatus and method for the insertion of an intravaginal article that is prepackagable in a sterile package.

It is a still further object of the invention to provide an apparatus and method for the insertion of an intravaginal article that is simple and inexpensive and readily adaptable to commercial use.

Other objectives of the present invention will be apparent from the following detailed description of the preferred embodiments.

SUMMARY OF THE INVENTION

In accordance with the present invention, an apparatus for the insertion of an intravaginal article into a mammalian female is provided which comprises a sleeve, a transmitter tube movably received within the sleeve, and a release means adapted to release an intravaginal article from the tube. An anterior portion of the sleeve is adapted to be inserted within a segment of the reproductive tract of the female that is adjacent to the vulva and an anterior portion of the tube is adapted to be inserted within the tract to a point deeper within the tract than the segment adjacent to the vulva, such that contaminants in the segment are not carried to the deeper point by the tube. The invention also comprises an apparatus for insertion of an intravaginal article into a mammalian female that includes a transmitter tube and a plunger movably received within the tube and longer than the tube, wherein an anterior end of the tube is releasably fixed in a closed, wedge-shaped position, such that an anterior portion of the tube is adapted to be inserted within the reproductive tract of the female and wherein the end is openable by means of the exertion of pressure from the inside of the tube, such that the tube is adapted to release an intravaginal article by pushing the article through the anterior end with the plunger. The invention also includes methods for inserting intravaginal articles.

BRIEF DESCRIPTION OF THE DRAWINGS

FIG. 1 is a perspective view of an assembled apparatus for inserting an intravaginal article, in accordance with the invention.

FIGS. 2 through 6 are perspective views of disassembled parts of the apparatus depicted in FIG. 1.

FIG. 7 is a perspective view of the apparatus prior to use and packaged in a sterile container.

FIG. 8 is a cross-sectional view of a reproductive tract of a mammalian female, depicting the use of the invention.

DESCRIPTION OF THE PREFERRED EMBODIMENTS

The need in the art for an improved apparatus for inserting an intravaginal article is satisfied in the present invention. The invention provides a means for safely and efficiently introducing intravaginal articles while reducing the opportunity for infection and reducing the discomfort experienced with the use of prior art apparatus. The invention can be used for the insertion of all types of intravaginal articles, including electronic and mechanical devices, medicines, bio-affecting substances, tampons and the like. Specific examples of multifunctional devices that can be inserted with the present apparatus include those described in U.S. Pat. No. 4,377,157 and the co-pending application of David L. Zartman, entitled "Intravaginal Anchor" and filed concurrently herewith and hereby incorporated by reference.

The nature of the invention can be more fully appreciated by reference to the appended drawings, in which a preferred embodiment is depicted. As depicted in FIG. 1, it can be seen that the assembled apparatus 10 consists of an outer sleeve 12, an inner sleeve or transmitter tube 14 and a plunger 16. Sleeve 12 is tubular in shape and transmitter tube 14 is provided with an exterior diameter that is somewhat smaller than the interior diameter of sleeve 12, such that the transmitter tube is movable longitudinally while being received by sleeve 12. Transmitter tube 14 is longer than sleeve 12 such that a relatively large anterior portion 18 extends beyond an anterior end 20 of sleeve 12 and a relatively small posterior portion 22 extends beyond a posterior end 24 of sleeve 12.

Plunger 16 is adapted to release an intravaginal insert from tube 14. It is longer than tube 14, such that an anterior end 26 of the plunger extends beyond an anterior end 28 of the tube, while a posterior portion 30 of the plunger extends beyond posterior end 32 of the tube. The interior diameter of tube 14 is somewhat larger than the exterior diameter of plunger 16, such that the plunger is movable longitudinally while being received by tube 14. The plunger may be of solid or hollow construction, but a solid, planar anterior face 34 is provided in a preferred embodiment so that sufficient contact is made between the face and an intravaginal article that is placed thereupon and pushed with the plunger.

As more clearly depicted in FIGS. 2 through 5, the anterior end 20 of sleeve 12 and the anterior end 28 of tube 14 are releasably fixed in a wedge-shaped, closed position in a preferred embodiment prior to use. The wedge shape can be established in a number of ways, the important characteristic being that of streamlining the anterior ends of the apparatus that will be inserted into the reproductive tract of the recipient animal, such that the process is more comfortable for the animal and safer for both the animal and the farm worker. The releasable closing of anterior end 20 of sleeve 12 also assists in preventing contaminants located in the region of the vulva from reaching the tube 14.

In FIG. 2, the wedge shape of sleeve 12 has been provided by pinching anterior end 20 to form curved lip 36. A piece of tape 38 has been added to secure the end in its closed position, and is selected to release the two sides of the lip when tube 14 is moved towards and through end 20. The release of the end by tape 38 can be effected by the breaking of tape 38 or by release of the tape from at least one side of sleeve 12.

As depicted in FIGS. 3 through 5, the wedge-shaped, releasably closed end 28 of tube 14 is formed in a somewhat different fashion. As depicted in FIG. 3, four slots 40, two of which are shown, are cut longitudinally from anterior end 28. Notches 42, 44 are cut between two pairs of the slots. As depicted in FIG. 4, peripheral flanges 46 are then folded over on central flanges 48 on either side of tube 14. Finally, as depicted in FIG. 5, a piece of tape 50, similar in characteristics to tape 38 depicted in FIG. 2, is affixed to releasably close anterior end 28, such that anterior end 28 can be opened by moving an anterior end 26 of plunger 16 towards and through anterior end 28.

In particular, an anterior portion 52 of sleeve 12, as depicted in FIG. 2, is inserted within a segment of the reproductive tract of the recipient mammalian female that is adjacent to the animal's vulva. Anterior portion 52 extends a sufficient distance into the segment of the reproductive tract such that portion 52 traverses the area in which pathological contaminants commonly associated with the exterior regions of the animal's reproductive tract are found. In the case of cattle and horses, an anterior portion 52 having a length of about 6 to 9 cm is satisfactory. The anterior portion is separated from a posterior portion 54 by collar 56, which defines the depth of penetration of the apparatus into the tract. Posterior portion 54 serves as a handle or grip that facilitates manipulation of the apparatus. When tube 14 is received within sleeve 12, as depicted in FIG. 1, posterior portion 22 of tube 14 extends beyond posterior end 24 of sleeve 12 and acts as a second handle or grip. Together, the grip of the sleeve and the grip of the tube provide precise maneuverability of the tube.

The dimensions of sleeve 12, tube 14, and plunger 16 vary depending upon the age and mammalian family of the animal to which the apparatus is applied, as well as the size of the intravaginal article that is to be inserted. The article should be capable of moving freely within tube 14 and, in order to eliminate any unnecessary discomfort, tube 14 is preferably no larger than is necessary to allow the free passage of the article within the tube. Thus, the interior diameter of tube 14 is preferably only slightly larger than the greatest exterior diameter of the article when the article is configured for insertion. The diameter of plunger 16 is preferably only slightly smaller than the interior diameter of tube 14. The interior diameter of sleeve 12 is preferably only large enough such that tube 14 can move freely therewithin.

The length of transmitter tube 14 and plunger 16 is primarily determined by the depth to which it is desired to insert the intravaginal article. The tube is long enough so that, when anterior end 28 of tube 14 is appropriately positioned for the delivery of the intravaginal article, posterior portion 22 extends beyond posterior end 24 and acts as a grip for the tube. Similarly, plunger 16 is preferably of such a length that, when appropriately positioned to release the article in a desired location, posterior end 30 protrudes beyond posterior end 32 of tube 14.

The apparatus is manufactured from a variety of materials, including metal, paper, cardboard, or plastic, such as nylon, or any combination of these materials. Food grade nylon is used in a preferred embodiment. The outer surface of the various parts of the apparatus are preferably smooth in order to avoid abrasion and irritation of the reproductive tract. In order to further lessen the possibility of abrasion or irritation, a suitable lubricant is applied to the surfaces of the apparatus that contact the reproductive tract, and such application can be made by the user at the time of insertion or by the manufacturer when the apparatus is packaged.

A particularly preferred feature of the materials used in manufacturing the apparatus is their sterilizability.

The apparatus is preferably sterilized prior to use by methods that include autoclaving, immersion in antiseptic solutions such as alcohol, exposure to toxic gas such as ethylene oxide, and irradiation, or a combination of these sterilization methods. Irradiation is preferred unless the intravaginal article comprises sophisticated electronic equipment that is subject to damage from radiation. In one embodiment, the apparatus is sterilized immediately prior to use, and, in a preferred embodiment, the apparatus is sterilized by the manufacturer and packaged in a sterilized bag or other suitable container. Another preferred feature of the materials is that they be inexpensive, so that it is economical to dispose of the apparatus after a single use.

In FIG. 7, the apparatus is depicted in a preferred embodiment prior to use. Here, the entire apparatus has been sterilized by the manufacturer and sealed in a sterilized package 60. Although a number of arrangements of the various parts within a package are possible, the arrangement depicted in FIG. 7 allows immediate and convenient insertion. When packaged in this fashion and composed of disposable materials, the temptation to reuse the apparatus without sterilization is diminished, and the likelihood of disease transmission from animal to animal is correspondingly reduced. In the embodiment depicted in FIG. 7, plunger 16 is disposed within tube 14 which is in turn disposed within sleeve 12. The anterior ends 20, 28 of the sleeve and tube are releasably fixed in a wedge-shaped, closed position. Adjacent to anterior end 28 and within tube 14 is an intravaginal anchor 62. The anchor is disposed in a collapsed position, as is fully described in the aforementioned copending application entitled "Intravaginal Anchor" and carries one of a number of possible payloads. Anterior end 26 of plunger 16 is disposed adjacent to posterior end 64 of the intravaginal anchor. A lubricant is already applied by the manufacturer and, in order to prepare the apparatus for use, it is merely necessary to remove the apparatus from the package.

The use of the device is depicted in FIG. 8. There, the reproductive tract 66 of a cow is depicted. The tract consists of, most posteriorly, the animal's vulva 68, vagina 70, cervix 72, and the uterus 74. Vagina 70 comprises a relatively narrow posterior portion 76 and a relatively broad anterior portion 78, and may be constricted by muscle contractions, such as contraction 80.

Before inserting the apparatus, a non-irritating lubricant is preferably sprayed or spread onto the lips of the vulva of the recipient female. If the apparatus has not been prelubricated, it is also preferable to spray or spread the lubricant on those parts of the apparatus that will come into contact with the walls of the reproductive tract. The lips of the vulva are then spread and the anterior end 20 of sleeve 12 is then gently introduced until all of anterior portion 52 is received in the segment 82 of the reproductive tract that is adjacent to the vulva. At this point, collar 56 rests against vulva 68 to prevent the further passage of sleeve 12 into the reproductive tract.

After sleeve 12 is properly positioned, tube 14 is forcefully moved forward until its anterior end 28 passes through anterior end 20 of sleeve 12. In the preferred embodiment, anterior end 20 will have been releasably fixed in a wedge-shaped, closed position, and the forceful movement of tube 14 causes anterior end 20 to open. At this point, the operator will be able to manipulate the apparatus by gripping posterior portion 54 of sleeve 12 with one hand and posterior portion 22 of tube 14 with the other.

Tube 14 is then moved forward through posterior portion 76 of the vagina. In a preferred embodiment, wherein an intravaginal device 62 is to be inserted into the deep vagina 84, the forward movement of tube 14 is continued until a resistance is felt when anterior end 28 contacts cervical wall 86. At this point, the operator backs tube 14 out of the vagina a small distance and, if the intravaginal article was not prepackaged within tube 14, as depicted in FIG. 7, then the intravaginal article is inserted into posterior end 32 of tube 14 at that time. Another method for inserting tube 14 to a desired point involves the use of marking 90. The marking can be made in accordance with known vaginal dimensions of the recipient animal such that, when the tube is inserted to a depth at which marking 90 is aligned with posterior end 24 of sleeve 12, tube 14 will be appropriately positioned.

When the tube 14 is correctly positioned and the intravaginal article 62 is in place in the tube, plunger 16 is moved forward so that intravaginal device 62 is expelled from anterior end 28 of the tube 14. In the preferred embodiment, anterior end 28 is releasably fixed in a wedge-shaped, closed position, such that the forward movement of device 62 causes the seal to be released and the end to open. A suitable marking 92 is used in one embodiment to assist the operator in inserting the plunger 16 to a desired depth, wherein the marking is aligned with posterior end 32 of tube 14. Preferably, the operator maneuvers the apparatus such that tube 14 is backed out as intravaginal device 62 slides into position.

It is desirable in certain circumstances to inspect the reproductive tract of the animal before the apparatus is removed. In these circumstances, the operator simply removes plunger 16 and clips a small flashlight or other source of illumination inside of the tube 14 adjacent to posterior end 32. This enables visual inspection of the reproductive tract which can be important in assessing the condition of the tract and in discovering any structural abnormalities such as cervical malformations that might render artificial insemination difficult. Following the optional inspection step, the apparatus is simply removed from the animal and, in the preferable disposable embodiment, discarded.

While a particular embodiment has been described above in connection with emplacement in a cow, it is to be understood that the apparatus is suitable for use in connection with all mammalian females, including but not limited to those of the bovine, ovine, caprine, equine, and porcine families, as well as humans. Examples of human applications for the apparatus are those involving the monitoring of deep body temperature, enhancement of fertility and avoidance of pregnancy.

While an especially preferred embodiment of the invention comprises the features of sleeve 12, transmitter tube 14 and plunger 16, embodiments comprising less than all of the inventive features remain within the scope of this invention. Thus, in one embodiment, sleeve 12 is eliminated, especially in the case where there is no likelihood of contamination on the exterior surfaces of the reproductive tract. In this embodiment, the insertion of tube 14 is facilitated by releasably fixing anterior end 28 in a wedge-shaped, closed position, as described above. In a second embodiment, the releasably fixed, wedge-shaped, closed positions of anterior ends 20 and 28 are eliminated, but contamination is prevented by the provision of sleeve 12 around tube 14, as described above.

In order to further illustrate the invention, the following specific examples are set forth.

EXAMPLE I

An intravaginal anchor provided with an instrument package, as described in the aforementioned application entitled "Intravaginal Anchor", was inserted into a Holstein heifer of breeding age. The apparatus was made of cardboard spools taken from rolls of paper towels and wrapping paper. A collar affixed centrally on the sleeve was made of cardboard also. The sleeve had an interior diameter of 4.44 cm and the tube had an interior diameter of 3.81 cm. The plunger had an outside diameter of 3.18 cm. Anterior ends of the tube and the sleeve were cut into a beveled shape, flattened, and taped shut to form a beveled tip. The sleeve was about 20.3 cm long and its collar was disposed 8.89 cm from the anterior end and had an outside diameter of about 8.89 cm. The tube was about 45.7 cm long and the plunger was about 58.4 cm long.

EXAMPLE II

Example I was repeated, except that the animal into which the apparatus was to be inserted was unruly. Accordingly, stiffening ribs were constructed around the longitudinal axis of the tube and sleeve to reduce the probability of bending.

EXAMPLE III

For insertion in a fully developed Holstein, an apparatus is provided with a vulva sleeve, transmitter tube and plunger. The vulva sleeve is 18 cm in length, 4.13 cm in exterior diameter, and provided with a centrally located collar. The collar has a diameter of 8.89 cm. The anterior end of the sleeve is folded and taped shut, and the tape is selected such that it breaks easily.

The transmitter tube is 50.8 cm in length and 3.81 cm in exterior diameter. Four 5.08 cm slots are cut at the anterior end of the tube. These slots are disposed in opposite pairs, the members of a pair being parallel and spaced 1.90 cm apart. Two notches are cut that separate the pairs of slots from each other. Peripheral flanges are folded over central flanges of the anterior end so that the anterior end is closed in a pointed fashion. The end is taped shut with a tape that breaks easily.

The plunger is 60.1 cm in length and 2.86 cm in exterior diameter. The anterior end of the plunger is plugged so that it is capable of exerting a pressure against an intravaginal device disposed within the tube.

It will be apparent to those skilled in the art that many modifications and variations may be introduced without departing from the inventive scope of the present teachings.

I claim:

1. An apparatus for insertion of an intravaginal article into a mammalian female, said apparatus comprising
    a sleeve having an anterior end and a posterior end, said anterior end being releasably closed,
    a tube having an anterior end and a posterior end and being movably received within said sleeve, wherein a force caused by a movement of said anterior end of said tube towards said anterior end of said sleeve opens said anterior end of said sleeve, and
    a release means adapted to release an intravaginal article from said tube,
    wherein an anterior portion of said sleeve is of such a length as to be insertable within a segment of the reproductive tract of said female that is adjacent to the vulva and an anterior portion of said tube is of such a length as to be insertable within said tract to a point deeper than said segment, such that, when so inserted, contaminants in said segment are not carried to said deeper point by said tube.

2. The apparatus of claim 1 wherein said release means comprises a plunger that is longer than said tube, movably received within said tube, and adapted to cause the release of said intravaginal article by pushing said article through said anterior end of said tube.

3. The apparatus of claim 2 wherein said anterior end of said tube is releasably closed in a wedgeshape, wherein a force caused by a movement of an anterior end of said plunger towards said anterior end of said tube opens said anterior end of said tube.

4. The apparatus of claim 1 wherein said anterior end of said sleeve is releasably closed in a wedge shape.

5. The apparatus of claim 1 wherein a posterior portion of said sleeve that is not inserted within said tract forms a grip.

6. The apparatus of claim 1 wherein said sleeve is provided with a collar disposed between said anterior portion of said sleeve and a posterior portion of said sleeve that is not inserted into said tract.

7. The apparatus of claim 1 wherein said tube comprises a grip and is adapted such that, when said anterior portion of said tube is inserted to said point deeper within said tract, said grip extends from a posterior end of said sleeve.

8. The apparatus of claim 1 wherein said tube is further adapted to releasably retain said article adjacent to an anterior end of said tube.

9. The apparatus of claim 1 wherein said point deeper within said tract is disposed within an anterior portion of said vagina.

10. The apparatus of claim 1 further comprising a sterilized package, wherein at least said sleeve, tube and release means are releasably enclosed within said package.

11. A method for inserting an intravaginal article within the reproductive tract of a mammalian female comprising the steps of
    selecting an inserting apparatus having a sleeve, a tube movably received within said sleeve, and a release means adapted to release said article from said tube,
    positioning said tube such that an anterior end of said tube does not extend beyond an anterior end of said sleeve,
    inserting said sleeve within a segment of the reproductive tract that is a distance from the cervix and adjacent to the vulva,
    moving said tube forward such that its anterior end passes through said anterior end of said sleeve and to a point deeper in said reproductive tract than said segment, and
    releasing said article from said tube.

12. The method of claim 11 wherein said moving step comprises moving said anterior end of said tube to a point within an anterior portion of said vagina.

13. The method of claim 11 wherein said releasing step comprises the step of inserting a plunger through said tube to push said article through said anterior end of said tube.

14. The method of claim 11 further comprising the step of releasably closing said anterior end of said sleeve in a wedge shape prior to said inserting step, wherein said moving step comprises opening said closed anterior end of said sleeve with a force caused by the moving forward of said tube.

15. The method of claim 13 further comprising the step of releasably closing said anterior end of said tube in a wedge shape prior to said inserting step, wherein said inserting step comprises opening said closed anterior end of said tube with a force delivered by said article.

16. The method of claim 11 wherein, following said moving step, a posterior portion of said sleeve extends beyond said reproductive tract and a posterior portion of said tube extends beyond a posterior end of said sleeve, said method further comprising the step of positioning said anterior end of said tube prior to said releasing step by manipulating said posterior portions of said sleeve and tube.

17. The method of claim 11 further comprising the step of inspecting interior walls of said tract by providing illumination at a posterior end of said tube and viewing said walls through said tube.

18. A method for inserting an intravaginal article within the reproductive tract of a mammalian female comprising the steps of selecting an insertion apparatus having a sleeve, a tube movably received within said sleeve, and a release means adapted to release said article from said tube, positioning said tube such that an anterior end of said tube does not extend beyond an anterior end of said sleeve, releasably closing said anterior end of said tube, inserting said sleeve within a segment of the reproductive tract that is a distance from the cervix and adjacent to the vulva, moving said tube forward such that its anterior end passes through said anterior end of said sleeve and to a point deeper in said reproductive tract than said segment, and releasing said article from said tube by inserting a plunger through said tube to push said article through said anterior end of said tube, whereby said closed anterior end of said tube is opened with a force delivered by said article.

* * * * *